US00PP11312P

United States Patent [19]

Whitcomb

[11] Patent Number: Plant 11,312

[45] Date of Patent: Mar. 28, 2000

[54] CRAPE MYRTLE PLANT NAMED 'WHIT V'

[76] Inventor: Carl E. Whitcomb, Rte. #3, Box 135, Stillwater, Okla. 74076

[21] Appl. No.: 09/032,259

[22] Filed: Feb. 27, 1998

[51] Int. Cl.[7] ..... A01H 5/00

[52] U.S. Cl. ..... Plt./252

[58] Field of Search ..... Plt./252

*Primary Examiner*—Howard J. Locker

*Attorney, Agent, or Firm*—Crowe & Dunlevy; Bill D. McCarthy; Phillip L. Free, Jr.

[57] ABSTRACT

A new and distinct variety of crape myrtle, *Lagerstroemia indica,* which is characterized by a low, dense, mounded shrub form that may reach three to four feet in height and width with age; stiff, ruby red young branches; ruby red new leathery foliage which quickly changes to green with age; crimson to ruby red flower buds; currant red to light red flowers; and no seed production. The new variety is also characterized by a long bloom period.

2 Drawing Sheets

BACKGROUND OF THE INVENTION

1. Field of the Invention

The present invention relates to a new and distinct variety of cultivar of the ornamental shrub, *Lagerstroemia indica,* commonly known as crape myrtle.

2. Description of the Prior Art

The crape myrtle shrub is native to eastern China and was introduced into North America in the late 1700s. Since then, this popular ornamental shrub has been grown extensively throughout the continent. Over the years, seedlings and hybrids between *L. indica* and *L. fauriei,* have been selected for various growth forms, flower colors, or other features and propagated asexually. An assortment of methods have been utilized in attempting to develop improved varieties of crape myrtles, at least several of which have had U.S. Plant Pats. issued.

For example, U.S. Plant Pat. 4,182, U.S. Plant Pat. 4,183, U.S. Plant Pat. 4,184, and U.S. Plant Pat. 4,185 disclose and claim a series of four new varieties of *Lagerstroemia indica* produced by crossing previously known varieties. Each of these new varieties was characterized as having a weeping growth habit at maturity. U.S. Plant Pat. 5,302 also discloses a new variety of crape myrtle exhibiting a weeping growth habit at maturity.

U.S. Plant Pat. 6,365 discloses a variety of crape myrtle derived from seedlings that had been treated with a mutation inducing chemical. The plant was characterized as having variegated pink flowers bordered by pure white and flowering over an extremely long period of time.

It is generally known that ethylmethane sulfonic acid methyl ester, EMS, is capable of producing plant mutations. EMS sometimes induces partial or complete sterility in the mutant plant and the mutants often have thicker than normal leaves and variegated flowers, with an occasional flower that is a solid color among the predominantly variegated flowers. The new variety of crape myrtle of the present invention may be such a mutant.

SUMMARY OF THE INVENTION

The present invention involves the discovery of a new and distinct variety of crape myrtle, *Lagerstroemia indica,* which has been given the cultivar name 'Whit V' and which is characterized by a low dense shrub form that may reach three to four feet in height and similar width with age. The leaves of the plant are ¼ to ½ the size of the species average and more leathery, emerging ruby red and soon change to pale green, then to dark green. Inflorescences are small relative to the species average but prolific. Flower buds are crimson. Flowers typically are in clusters of three to ten or more or sometimes singly and more or less evenly distributed over the plant. Individual petals are a light red with an occasional white petal or petals on a flower. During hot summer days the flowers are more intense in color, whereas on cooler, overcast days the flower color is less intense. Flowering generally begins early in the season relative to other crape myrtle varieties, e.g. mid July in north central Oklahoma, but flowering continues until frost. To date no seeds have been produced either on the original plant or offspring propagated from softwood cuttings. By contrast, many varieties of crape myrtle plants bloom heavily in July or August, set a heavy seed crop and flower sparingly, if at all, for the rest of the growing season.

DESCRIPTION OF THE VARIETY

The new variety of crape myrtle, which has been give the cultivar name 'Whit V' was selected from over 65,000 seedlings grown from an original seedling plant that had been selected because of the dark foliage and near red flowers and produced large quantities of seeds with good germination and seedling vigor. Prior to planting, the seeds were treated with ethylmethane sulfonic acid methyl ester, EMS, which is generally known to be capable of producing plant mutations. Treated seeds were planted in flats in the greenhouse. After the seeds germinated, the seedlings were transplanted into small containers and mildew was introduced from susceptible seedlings in large containers. Seedlings susceptible to mildew or with poor vigor were rogued out and the remainder of the seedlings were planted in rows in an open field for further evaluation. The new variety was selected from the population in the field for the unique growth habit; dense, stiff branching; foliage and flower color. It may be a mutant seedling arising from the EMS treatment as it does have an occasional bicolor flower and has produced no seeds to date and has leathery leaves. The original asexual propagation took place in a field in north central Oklahoma from softwood cuttings. The new variety has been faithfully reproduced by such means.

Softwood cuttings taken from the original plant have been successfully rooted in a medium of peat and perlite under intermittent mist. Subsequent cuttings taken from plants resulting from previous cuttings have been similarly rooted. Growth, branching habit, flowering, and flower, foliage and branch color remain consistent with the original plant.

A detailed description of the new variety of crape myrtle follows:

Parentage: Selected from over 65,000 crape myrtle seedlings grown from a selected seedling plant. The seeds were treated with EMS to induce mutations. The occasional variegated flowers, thick, leathery leaves, and lack of seed production are indications that the new variety may be a mutant seedling.

Growth: The plant roots easily from softwood cuttings, shows no adverse effects from transplanting and grows by producing a multitude of short branches. In north central Oklahoma, softwood cuttings taken in June root in about 20 days and when transplanted into a one-gallon (six-inch diameter) container result in plants full and thick, approximately eight inches tall and 10 inches in diameter by late September with no pruning. Height with age may reach three to four feet with a similar or slightly greater horizontal spread. Unlike U.S. Plant Pats. 4182, 4183, 4184, 4185, and 5302 by Chopin, which have a weeping growth habit, my new crape myrtle plant branches profusely and the branches are stiff and do not weep.

Figure 1:
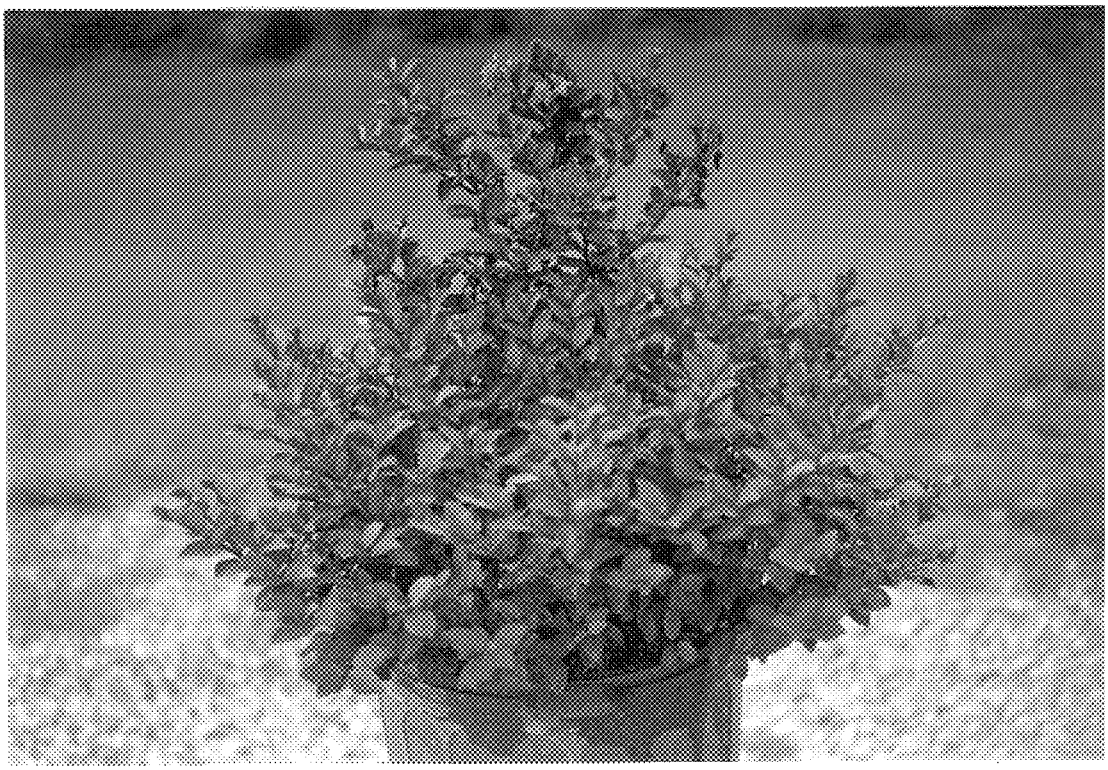
FIG. 1 is a photographic view of my new crape myrtle shrub in full color showing the general form and arrangement of a typical plant.
Figure 2:
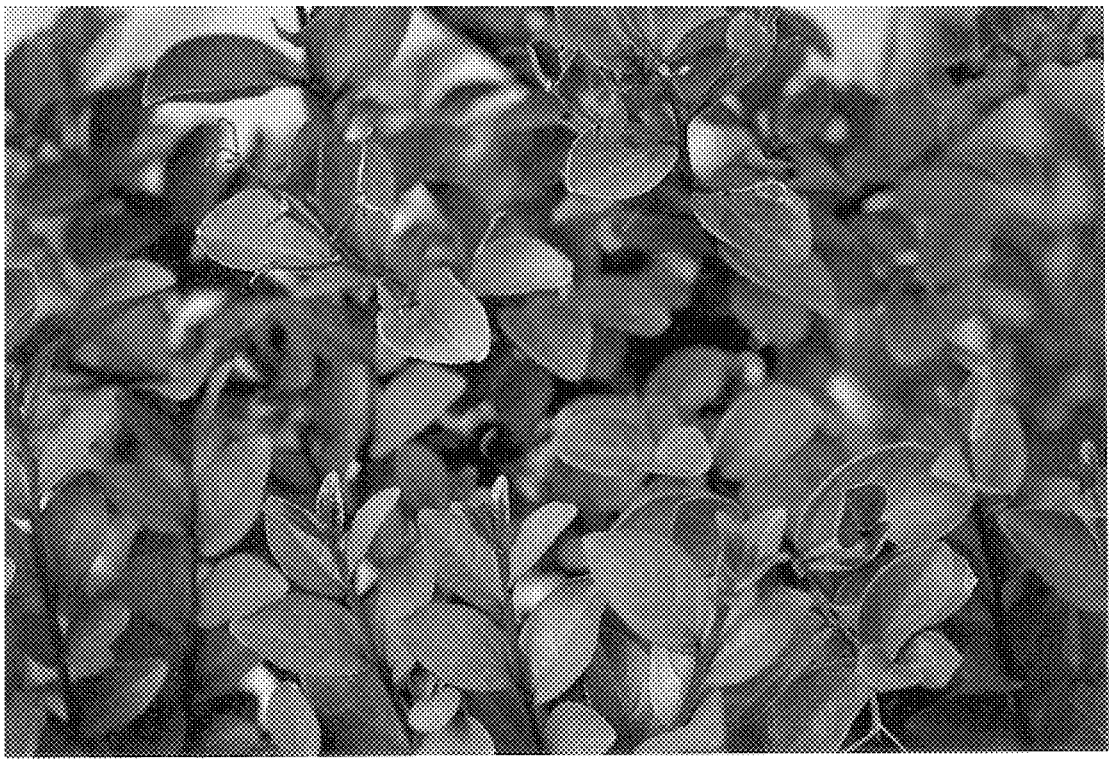
FIG. 2 is a photographic view in full color of the young branches and new, maturing, and old foliage of the shrub of FIG. 1, showing the new growth and the progression of color change as the leaves age as well as the old inflorescence absent seed pods.

Branches: Young branches are ruby red, red group 59—A and CIE coordinates .455, .282, 5.6 (color notations from The Royal Horticulture Society Colour Chart, 1966 and the Commission International de l'Eclairage 1931) and slowly change to a light tan with age. The ruby red young branches provide a contrast to the mature dark green leaves (FIG. 2).

Foliage: Leaves are about ¼ to ½ the size of the species average, and are typically from ½ inch to 1½ inches long, thick and leathery with maturity and with excellent retention, even during drought. New leaves emerge ruby red, 59—A (R.H.S.) and CIE .455, .282, 5.6 and gradually change to arras green, 139—A, (R.H.S.) and CIE .292, .400, 6.4 or 139—B (R.H.S.) and CIE .311, .417, 16.0 with maturity. Foliage color varies with light intensity, fertility, and growing conditions. Foliage has been very resistant to powdery mildew.

Bark: The bark is typical of the species and is exfoliating.

Figure 3:
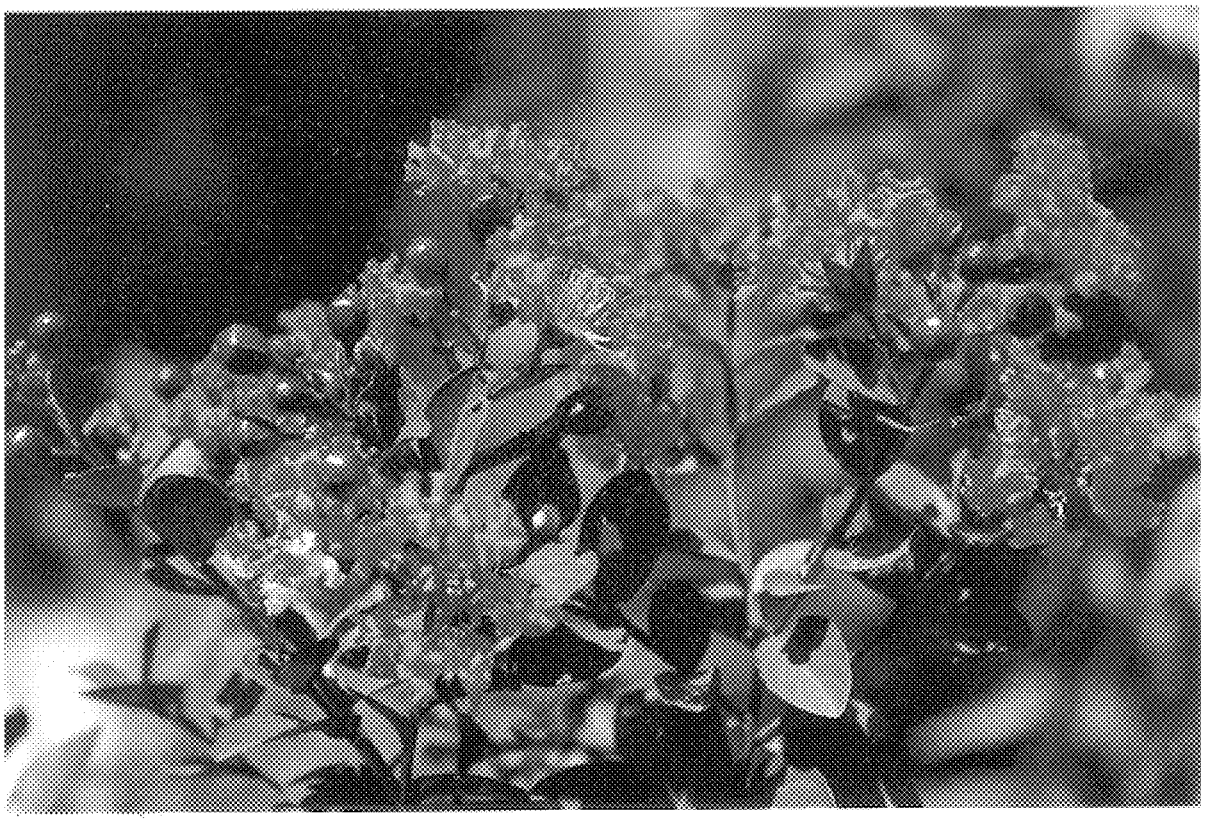
FIG. 3 is a photographic view in full color of flowers and flower buds of the shrub in FIG. 1.

Flowers: Flower buds are ruby red, 59—A (R.H.S.) and CIE .455, .282, 5.6. Individual petals are currant red, Red Group, 46—A (R.H.S.) and CIE .546, .310, 9.4 when flowers open on a sunny day but when flowers open on a cloudy day, flowers may be as light as 46—C (R.H.S.) and CIE .549, .315, 16.1. The presence of a flower with white margin is occasionally expressed (see FIG. 3) and varies with temperature, light intensity, and growing conditions. Individual flowers are of a size typical of the species and the yellow stamens are typically visible (FIG. 3). As the flowers age they generally fall cleanly without discoloring and becoming unattractive. The plant is sterile and the reproductive organs fall with the flower. The mechanism for sterility is currently unknown. As with other crape myrtle plants, the blooms each have six petals per bloom. Bloom diameter varies with environmental conditions. Pedicel coloration is that same as the petals and the length is typical of the species. The inflorescences are panicles. Flowers are more or less evenly distributed over the plant. In north central Oklahoma, flowering typically begins in mid July and continues sporadically until frost. A typical sequence is a flower show across the surface of the shrub (see FIG. 3) than the flowers drop cleanly (see FIG. 2) leaving no seed pods, then with another flush of growth, more flowers develop on the tips of the new branches. Flowers are typically in clusters of three to 10 or more or sometimes singly. To date no seeds have been produced either on the original plant or asexually propagated offspring.

Cold Hardiness: The new crape myrtle has withstood temperatures of 0 degrees F. but is killed to the ground at lower temperatures; however, regrowth in the spring is rapid and flowering resumes normally in July.

I claim:

1. A new and distinct variety of *Lagerstroemia indica,* crape myrtle plant substantially as shown and described and partially characterized by a dense rounded shrub form that may reach three to four feet in height with similar width with age; stiff, ruby red young branches; ruby red new foliage that quickly changes to green and with age becomes leathery; crimson to ruby red flower buds; currant red to light red flowers, no seeds, and with a long bloom period.

* * * * *